US007338796B1

(12) United States Patent
Davalos et al.

(10) Patent No.: US 7,338,796 B1
(45) Date of Patent: Mar. 4, 2008

(54) VESICLE-BASED METHOD AND APPARATUS FOR COLLECTING, MANIPULATING, AND CHEMICALLY PROCESSING TRACE MACROMOLECULAR SPECIES

(75) Inventors: Rafael V. Davalos, Oakland, CA (US); Christopher R. B. Ellis, Oakland, CA (US)

(73) Assignee: Sandia Corporation, Livermore, CA (US)

( * ) Notice: Subject to any disclaimer, the term of this patent is extended or adjusted under 35 U.S.C. 154(b) by 730 days.

(21) Appl. No.: 10/914,991

(22) Filed: Aug. 9, 2004

Related U.S. Application Data

(60) Provisional application No. 60/495,213, filed on Aug. 13, 2003.

(51) Int. Cl.
*C12M 1/42* (2006.01)
*C12N 13/00* (2006.01)
*B32B 5/02* (2006.01)

(52) U.S. Cl. ....................... 435/285.2; 422/81; 422/82; 435/173.6

(58) Field of Classification Search ............. 435/285.2, 435/173.6; 422/81, 82
See application file for complete search history.

(56) References Cited

U.S. PATENT DOCUMENTS 5,631,141 A * 5/1997 Sonek et al. .................. 435/29
6,570,196 B1 * 5/2003 Fromherz et al. ........... 257/213
2002/0182627 A1 * 12/2002 Wang et al. .................. 435/6
2003/0104588 A1 * 6/2003 Orwar et al. ............ 435/173.6
2004/0106189 A1 * 6/2004 Dodgson et al. ......... 435/285.2

OTHER PUBLICATIONS

Fischer, A.; Oberholzer, T; Luisi, P.L.;"Giant vesicles as models to study the interactions between membranes and proteins," *Biochimica et Biophysica Acta*, 2000, v. 1467, pp. 177-188.
Bucher, P.; Fischer, A.; Luisi, P.L.; Oberholzer, T; Walde, P.; "Giant Vesicles as Biochemical Compartments: The Use of Microinjection Techniques," *Langmuir*, 2002, v. 18, pp. 9259-9266.
Tsong T.Y.; "Electroporation of cell membranes," *Biophysical Journal*, 1991, v.60, pp. 297-306.
Chiu, D.T.; Wilson, C.F.; Ryttsén, F.; Strömberg, A.; Farre, C.; Karlsson, A.,; Nordholm, S.; Gagger, A.; Modi, B.P.; Moscho, A.; Garza-López, R.A.; Orwar, O.; Zare, R.N.;"Chemical Transformation in Individual Ultrasmall Biomimetric Containers," *Science*, 1999, v.283, pp. 1892-1895.
Davalos, R.; Huang, Y.; Rubinsky, B.; "Electroporation: Bio-Electrochemical mass transfer at the nanoscale," *Microscale Thermophysical Engineering*, 2000, v.4(3), pp. 147-159.
Ramos, C.; Teissié, J.; "Electrofusion: A biophysical modification of cell membrane and a mechanism in exocytosis," *Biochimie*, 2000, v.82, pp. 511-518.
Cummings, E.B.; "A comparison of theoretical and experimental electrokinetic and dielectrophoretic flow fields," *AIAA*, 2002, v.3193.

* cited by examiner

*Primary Examiner*—Walter D. Griffin
*Assistant Examiner*—Lydia Edwards
(74) *Attorney, Agent, or Firm*—Timothy P. Evans

(57) ABSTRACT

Disclosed is an apparatus and method for inserting one or several chemical or biological species into phospholipid containers that are controlled within a microfluidic network, wherein individual containers are tracked and manipulated by electric fields and wherein the contained species may be chemically processed.

10 Claims, 8 Drawing Sheets

VESICLE-BASED METHOD AND APPARATUS FOR COLLECTING, MANIPULATING, AND CHEMICALLY PROCESSING TRACE MACROMOLECULAR SPECIES

CROSS REFERENCE TO RELATED APPLICATIONS

This application claims priority to, prior now abandoned provisional U.S. Patent Application Ser. No. 60/495,213 entitled "VESICLE-BASED METHOD AND APPARATUS FOR COLLECTING, MANIPULATING, AND CHEMICALLY PROCESSING TRACE MACROMOLECULAR SPECIES," originally filed Aug. 13, 2003.

STATEMENT OF GOVERNMENT INTEREST

This invention was made with Government support under government contract no. DE-AC04-94AL85000 awarded by the U.S. Department of Energy to Sandia Corporation. The Government has certain rights in the invention, including a paid-up license and the right, in limited circumstances, to require the owner of any patent issuing in this invention to license others on reasonable terms.

FIELD OF THE INVENTION

The field of the invention comprises methods for processing and identifying trace quantities of macromolecular species, especially biological toxins, by using phospholipid vesicles as chemically processed containers or substrates that are manipulated within a microfluidic network.

BACKGROUND OF THE INVENTION

A critical dilemma facing chemical and biological toxin detection is in many instances only a very limited number of molecules may be available for analysis. Moreover, current methods are ill equipped or incapable of reliably concentrating and processing very small quantities of a target agent. Most rely on aerosol capture into a substrate fluid. Because of dilution and successive discarding of fluid, many molecules must be collected in order to provide an effectively concentrated solution with which to perform chemical analysis. Unfortunately, this can delay analysis for many minutes and/or lead to unreliable results. In addition, the number of molecules of interest may be limited and amplification of these molecules may not be an option. Therefore, the available sample must be neither wasted nor diluted and it must be processed in a manner capable of screening it from other species.

A method and apparatus is herein disclosed that combines the utility of several known technologies to address this problem. In particular, picoliter chambers comprising phospholipid vesicles about 1-20 microns in diameter, are used to manipulate and chemically process trace quantities of samples. These chambers are formed from synthetic lipids by well known methods, such as are described by Fischer, et al., (*Biochimica et Biophysica Acta,* 2000, v. 1467, pp. 177-188); and by Bucher, et al. (*Langmuir,* 1998, v. 14, pp. 2712-2721); or are created from preexisting cells (e.g. ghost red blood cells or "RBCs"). Due to their small size and composition, the vesicles serve as ideal biomimetic (i.e., human-made processes/devices/systems that imitate nature) nano-environments and provide for rapid, surface-functionalized chemical kinetics. Additionally, the vesicles are manipulated and moved through a fluidic network to specific locations where various reagents, analytes, proteins, or viruses are introduced into individual vesicles via electroporation, a well known technique in which the bilayer vesicle membrane is rendered temporarily porous under an applied electric field (see T. Y. Tsong, et al., *Biophysical Journal,* 1991, v. 60, pp. 297-306). Finally, successive electroporation steps allow multiple-part reactions to take place within the confines of a vesicle, and allow the localized release of products for analysis.

SUMMARY

It is therefore an object of this invention, to provide a micron sized, vesicle-based system, wherein the vesicle serves as a selectively permeable vessel into which a chemical or biological specie and one or more screening compounds are inserted into the vessel. The vesicle acts as a transport medium moving the reactants and reagents throughout a preparation and diagnostic analysis system.

It is an object of this invention to provide a microscopic liposome-like reaction chamber that can be moved, fused, or lysed with electric fields of varying magnitude and geometry.

It is yet another object of this invention to provide a multistage parallel "bio-foundry" within which a trace specie or compound is discretely tracked, manipulated and never lost.

It is another object of this invention to provide an on-chip biological analysis system wherein individual biological particles may be rapidly processed and identified.

It is yet another object of this invention to provide an entirely autonomous system that uses feedback control to manipulate, handle, and sort trace quantities of biological species.

These and other objects and advantages will become apparent to those having skill in these arts upon reading the following detailed description of the present invention, the drawings and the appended claims.

DETAILED DESCRIPTION OF THE INVENTION

The following terms of art are defined before providing a description and discussion of the present invention.

"Electroporation" refers to a process for rendering a lipid bilayer temporarily permeable or "porous" over a localized region. Electroporation occurs as a result of the reorientation of lipid molecules of the bilayer membrane to form hydrophilic pores in the membrane. The distribution of such pores, both in terms of size and number, determine the electrical properties of the cell membrane.

A "compound" is any material, sample or reagent that is intended to be controlled by being placed in a vesicle.

A "sample" consists of a solution of one or more macromolecules, such as proteins, enzymes, chemical toxins, or DNA or RNA fragments. A sample may also be a solution with whole bacteria, alive or dead or in spore form, or a solution containing viruses.

A "vesicle" is any aqueous volume surrounded by a single phospholipid bilayer membrane and may include synthetically produced liposomes, or altered preexisting cells (e.g., ghost RBCs). It is also a biomimetic nano-environment which will stimulate reactions that are available only in or on phospholipid bilayer membrane substrates. A vesicle measures up to 20 μm in diameter when suspended in an isotonic solution. A synthetic vesicle may be formed from a pure lipid composition or a mixture of lipids, cholesterols, and membrane proteins.

"Impedance measurement" involves either ac or dc applied voltages and sensing of transient or frequency-domain currents. Impedance measurements may happen before, during, and/or immediately after electroporation pulses.

Chemical analyses performed by separation processes such as chromatography are generally inefficient in that relatively large quantities of reagent materials are lost due to mixing, reacting, and moving of fluid. Of a diluted sample plug a small volume is used for electrophoretic separation, and the rest is discarded. To overcome these shortcomings, such systems have been greatly reduced in size but the apparatus channel lengths remain on the order of centimeters which equates to a about 0.1 μl of reagent per analysis if the column diameter is on the order of 100 microns.

Figure 1:
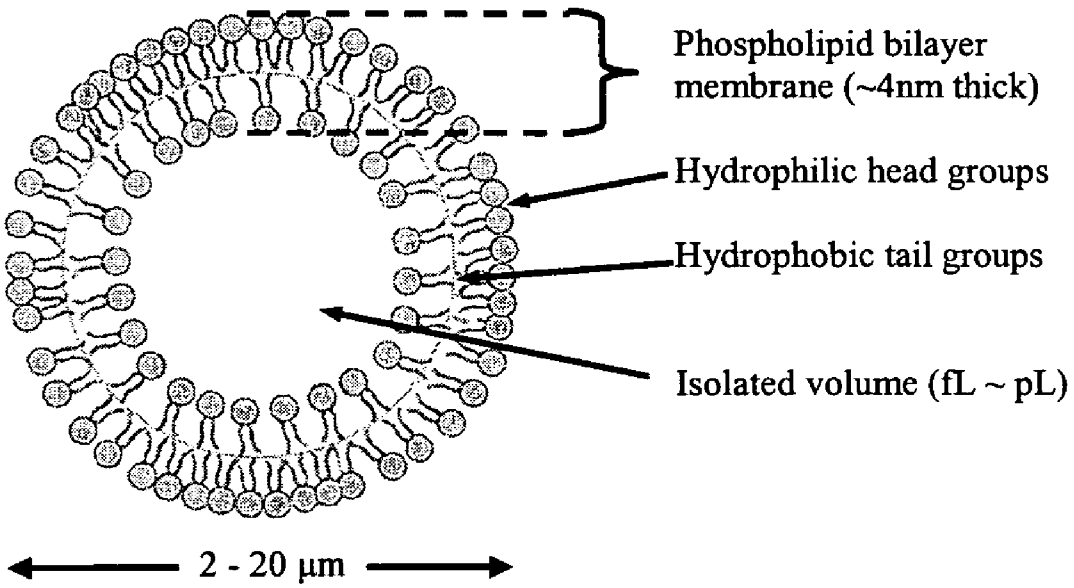
FIG. 1 shows a cartoon illustrating a typical vesicle in cross section.

Accordingly, an embodiment of the present invention comprises a vesicle-based microfluidic analysis network, wherein vesicles are used to move the sample and any reagent materials to the site of the separation column rather than moving the analyte through the entire length of the apparatus. The network comprises a micromachined chip intended to include multiple mobile picoliter storage chambers to manage front-end sample preparation prior to detection. Vesicles 1-20 μm in diameter, which are routinely used as tiny reaction vessels for in vitro studies, can serve as these portable chambers that may be selectively loaded with proteins or genetic material, analytes, and reagent and/or dye compounds (see D. T. Chiu, et al., *Science,* 1999, v. 283, pp. 1892-1895). Synthetic vesicles such as depicted in FIG. 1 are created from a solution containing synthetic lipids using a variety of techniques such as electroformation, mechanical extrusion, and rotary evaporation ("rotoevaporation").

Vesicle Formation

Vesicles can be created using a variety of techniques such as electroformation, mechanical extrusion, and rotoevaporation from a solution containing synthetic lipids, or by altering preexisting cells (e.g. ghost RBCs) (see P. Bucher, et al., *Langmuir,* 1998, v. 14, pp. 2712-2721). Vesicular containers are used to encapsulate compounds and prevent passage of compounds across the bilayer membrane to the surrounding medium. Compounds are only permitted to diffuse within the confines of the vesicle, and may not diffuse beyond the membrane. Samples within vesicles may be encouraged to mix rapidly due to the small vesicular volume. Reaction rate and thoroughness may be enhanced by confining reacting compounds to the small vesicular volume.

Vesicles need to meet certain basic criteria to be manipulable for autonomous sample preparation and for this particular example. A population's peak diameter needs to exceed 3 μm for immobilization, their membranes need to resist rupture while being held with negative pressure at a micro-aperture/channel portal, and the outermost membrane should not have encapsulated several internal liposomes, which could disrupt electroporation efficiency.

In order to prepare the desired vesicles, three different phospholipid materials were obtained (as powders) from Avanti Polar Lipids, Inc., Alabaster, Ala., and tested. The chosen compounds were 1,2-Dioleoyl-sn-Giycero-3-Phosphocholine (DOPC), 1,2-Dilauroyl-sn-Glycero-3-Phosphocholine (DLPC), and 1-Palmitoyl-2-10,12 Tricosadiynoyl-sn-Glycero-3-Phosphocholine (16:0-23:2 DIYNE PC). Solutions of each of these materials were prepared in both the virgin state and with between about 5 to about 20 mole %-cholesterol (also obtained from Avanti Polar Lipids, Inc.) added to the prepared solution mixtures, by mixing the lipid and cholesterol, as required, into a quantity of chloroform and 10 nM phosphate buffered saline ("PBS") having a pH of 7.4.

Of these, 16:0-23:2 DIYNE PC formed the most robust vesicles. The most successful composition found to date has been a mixture comprising 16:0-23:2 DIYNE PC and cholesterol in a 10:1 molar ratio. The liposome solution is prepared by combining 15 μL of 0.1M 16:0-23:2 DIYNE PC dissolved in chloroform with 1.5 μL of 0.1M cholesterol dissolved in chloroform. 980 μL of chloroform and 200 μL of methanol are then added to solution. Finally, a PBS/dye mixture prepared by combining 300 mL of 1 mg/mL Alexa Fluor 488 dye (chosen over the more common fluorescein FITC), for enhanced resilience to photo-bleaching) was dissolved in 6.7 mL of phosphate buffered saline (PBS) is added to the liposome solution, and the sample is connected to a rotary evaporator (Büchi Labortechnik AG, model R-205). Based on temperature, rotation speed, and vacuum, the chloroform and methanol are boiled off leaving a vesicle solution encapsulating PBS. The evaporation process requires about 15 minutes to complete and has successfully yielded a polydisperse solution with liposome diameters up to 10 μm. During this process, the liposome solution is rotated at 40 rpm under vacuum pressure at 40° C. Under these conditions, chloroform boils off at about 474 mbar, and methanol boils off at about 337 mbar. However, the solution is brought down to a final pressure of 90 mbar to ensure both solvents have completely evaporated off. Finally, the solution is polymerized via UV irradiation at 254 nm for 30 minutes to permanently cross-link the bilayer membrane.

Following polymerization the liposome solution is centrifuged once at about 2000 rpm for 30 minutes to concentrate the liposomes. The supernatant is removed, and the remaining centrifuged solids are re-suspended in phosphate buffered saline (pH 7.4).

Figure 2A:
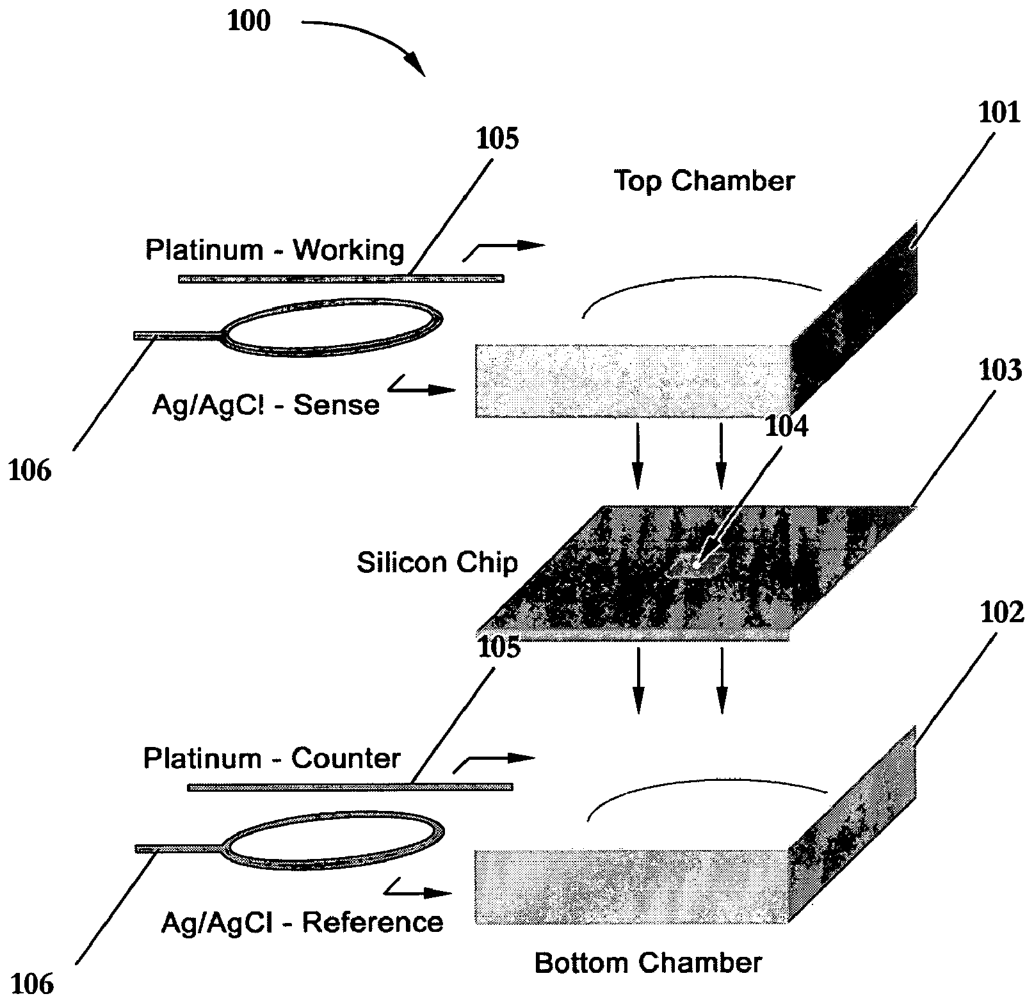
FIG. 2A shows an exploded schematic view of a test platform used as "proof-of-principle" to test electroporation of synthetic vesicles, made by the process of the invention, at a 6 micron micro-hole.
Figure 2B:
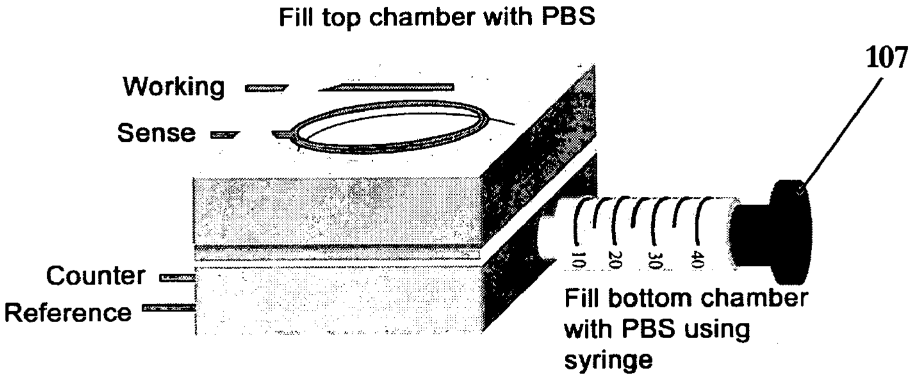
FIG. 2B shows a schematic view of the assembled test platform used as "proof-of-principle" to test electroporation of synthetic vesicles.

To study the process of vesicle manipulation and electroporation test platform 100 was constructed. Various views of the test platform are shown in FIGS. 2A and 2B, Similar to published single-cell electroporation, the device used low-level sensing voltages of 200 mV and permeation pulses up to 5 V. Impedance data with <1 ms time resolution is being acquired (See R. Davalos, et al., *Microscale Thermophys. Eng.,* 2000, v. 4(3), pp. 147-159).

Test platform 100 comprises a manifold that includes top and bottom chamber 101 and 102 and silicon "chip" 103 through which a 6 μm Ø micro-hole 104 is plasma-etched. Also included are one platinum working/counter electrode 105 and one Ag/AgCl sensing/reference electrode 106 on above and below silicon chip 103. Together, these four electrodes allow for accurate delivery and sensing of electrical signals (masking electrochemical events). When the manifold is assembled, silicon chip 103 containing micro-hole 104 separates chambers 101 and 102 and provides a volume into which a quantity of PBS (pH 7.4) solution and vesicles are introduced. A syringe 107 is attached to the lower chamber 102 and is used to draw a suction through micro-hole 103 in order to trap and hold a single vesicle and permit vesicle electroporation.

In this system most of the resistive impedance of the system exists across the micro-hole and mated vesicle. Because of this, any applied voltage drops almost entirely across the vesicle with the highest field strength across the vesicle membrane bridging the micro-hole. This is where we expect to see first onset of membrane permeation.

Figure 3:
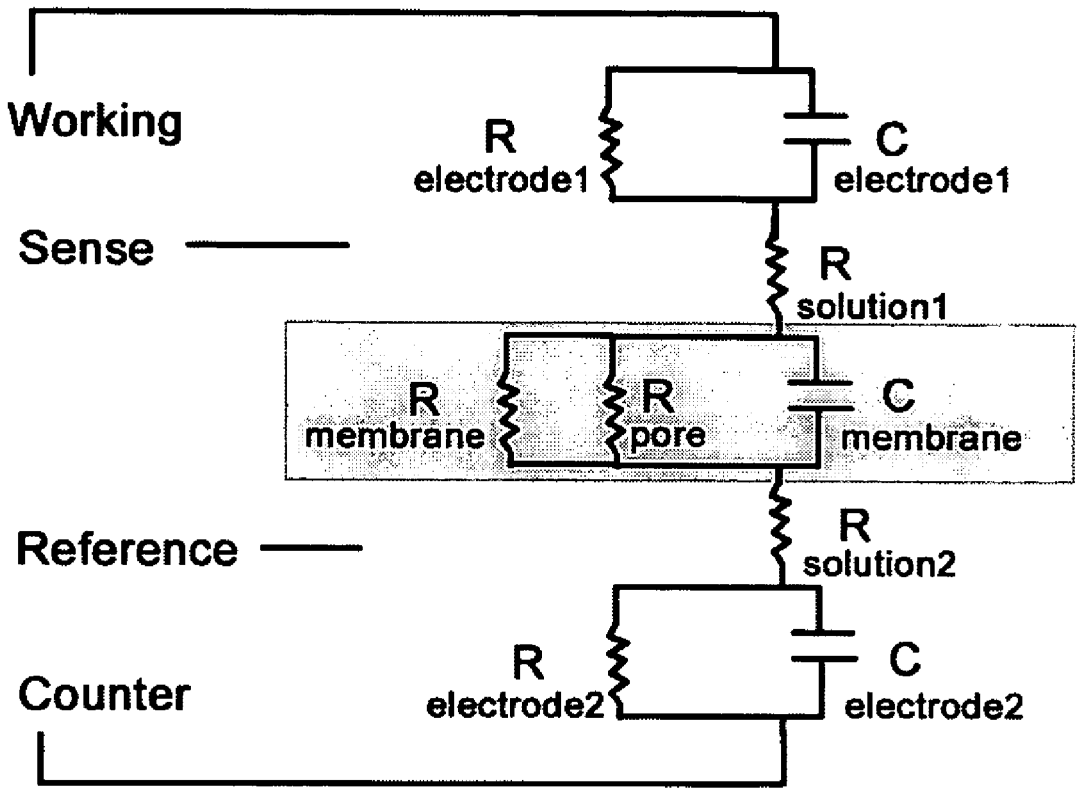
FIG. 3 shows a circuit schematic intended to simulate a vesicle held at the micro-hole of the test platform illustrated in FIG. 2.

Using a 200 mV sensing potential we measured the "open-circuit" micro-hole resistance to be between about 100 kΩ and 400 kΩ and the normalized vesicle impedance to be between about 400 kΩ and about 2 MΩ. We believe this range depends on either the tightness of the fluid seal between vesicle and surface adjacent to the micro-hole or the intrinsic transmembrane resistance of the vesicle itself. A simulated circuit diagram is shown in FIG. 3.

Membrane response to pulses can be categorized into three domains. Low amplitudes pulses of less than 500 mV do not cause appreciable permeation. Moderate pulses of 1 to 2 V with durations of between 10 to about 100 ms lead to membrane permeation and subsequent recovery, although occasionally trans-vesicle impedance never recovers to their original values. Larger pulses, e.g., 2 to 5 V with durations of between 10 to about 100 ms, induce unrecoverable vesicle membrane lysis.

Figure 4:
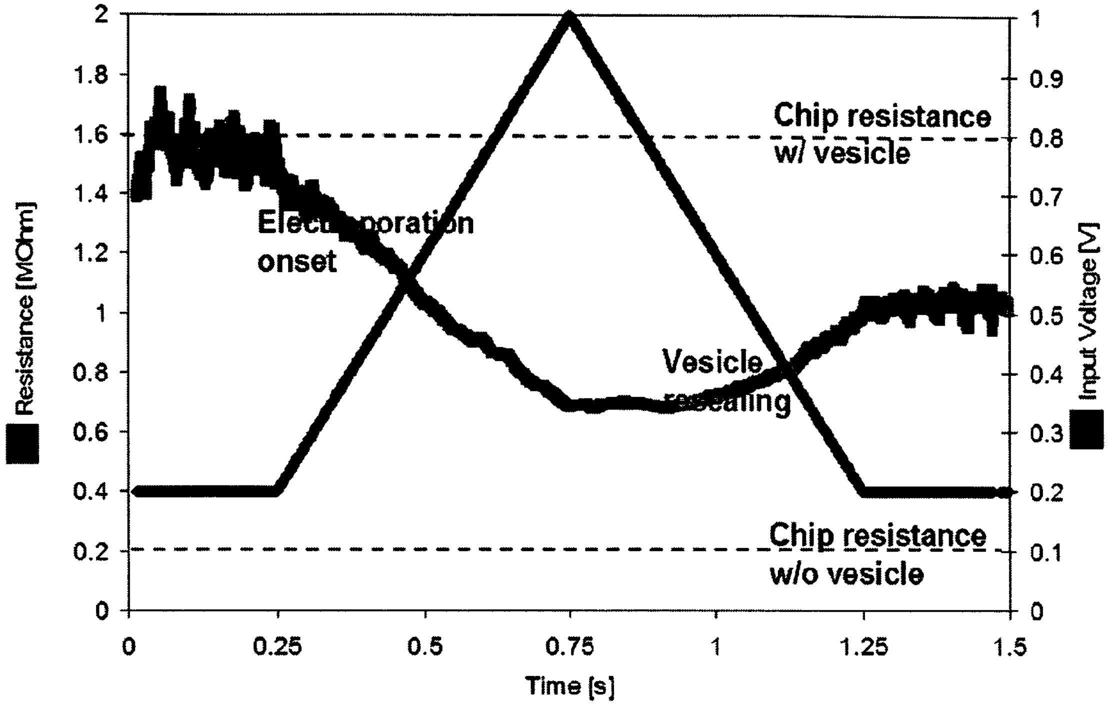
FIG. 4 shows the measured resistance of a vesicle held at the micro-hole of the test platform illustrated in FIG. 2 before and after the vesicle is subjected to a triangular voltage pulse of 1 volt.
Figure 5A:
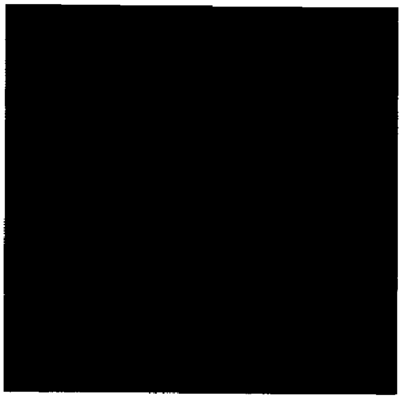
FIGS. 5A-D show a series of photomicrographs illustrating decay in the fluorescence of an Alexa Fluor 488-filled vesicle held at a micro-hole and exposed to several successive electroporation pulses.
Figure 5B:
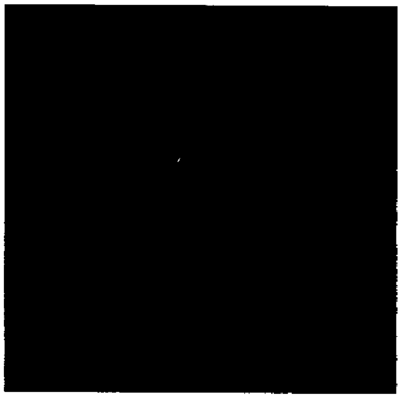
Figure 5C:
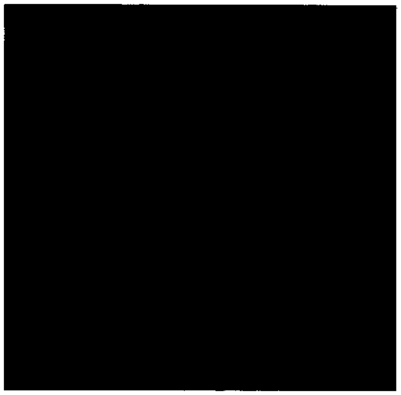
Figure 5D:
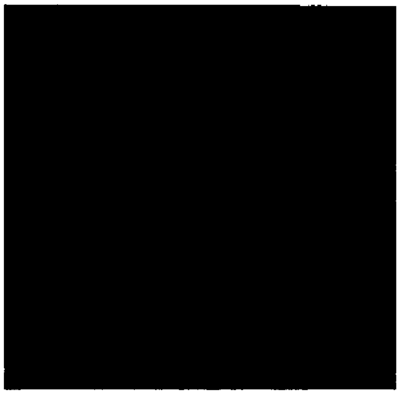

As shown in FIG. 4 a vesicle held at a micro-hole experiences a triangular voltage waveform. The impedance across the vesicle drops as the induced voltage increases, indicating pore formation. As voltage decreases the impedance recovers, indicating resealing of the membrane pores. The final resistance of the vesicle is lower than at the start which is believed to be evidence of irreversible electroporation.

Imaging the leakage of fluorescent dyes from the vesicles corroborates the impedance response of the vesicles. Alexa-Fluor 488 fluorescent dye was chosen for enhanced resilience to photo-bleaching and thus is less impacted by photo-polymerization during fluorometric imaging. Furthermore, an upper limit on Alexa-Fluor 488 concentration is set by its ability to self-quench. This dye was incorporated with PBS during the vesicle formation step and was thereby encapsulated within the vesicles. Centrifugation was then used to separate new—formed vesicles from the dye containing supernate.

As seen in FIGS. 5A-5D, that tests conducted with the entrapped Alexa-Fluor 488 dye showed that during electroporation at 2V with 100 ms pulses the fluorescence intensity of the vesicle decreases with each pulse. As noted earlier, in many cases the vesicle impedance remained much lower than its baseline level after a pulse strongly suggesting a destabilized membrane, although these liposomes retained dye for several minutes thereafter. Larger lysing pulses led to visible evidence of dye releasing to the surrounding region. Lysed membrane debris often accumulated around the micro-hole; after a few lysis events the hole clogged and the chip was removed for cleaning.

System Configuration

Figure 6:
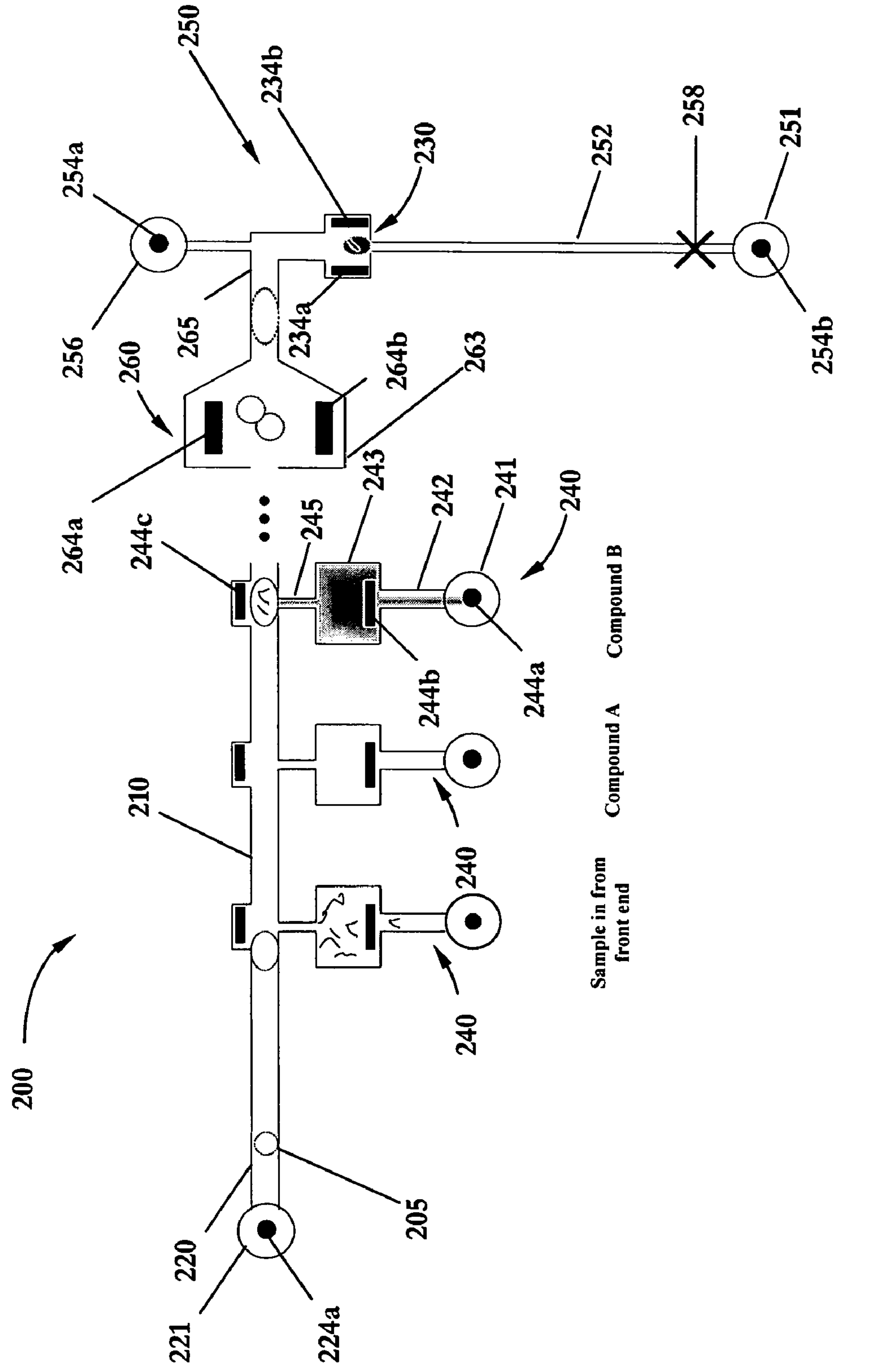
FIG. 6 shows a schematic of one embodiment of the microfluidic vesicle-based system of the present invention.

Referring now to FIG. 6, a preferred embodiment is illustrated and described as follows. A fluidic network 200 would comprise microchannel column 210 connected at one end to vesicle loading conduit 220 and at an opposite end by a vesicle unloading chamber 230 which is itself part of a microfluidic detection system 250 comprising buffer reservoir 256, separation column 252, waste reservoir 251, and field electrodes 254*a,b*. In addition, loading conduit 220 additionally comprises supply reservoir 221 and field electrode 224*a* for moving vesicles 205 into column 210. Similarly, vesicle unloading chamber 230 would include field electrodes 234*a,b* used to deliver low voltages for lysing vesicles 205.

In addition to the foregoing structures, fluidic network 200 would further comprise a plurality of branching stations, or compartments, 240 located between loading conduit 220 and unloading chamber 230, each of which would comprises a separate preloading chamber 243, a supply channel 242 connecting compartment 243 with a supply reservoir 241, a short small diameter inlet port (~2-6 μm) 245 connecting compartment 243 to microchannel column 210, and at least two electrodes 244*a* and 244*b* for electroporation and sensing. Additionally, microchannel column 210 would include "necked" constrictions (shown in FIG. 7A) just before compartments 240 in order to guide and help stabilize vesicles 205 as each is moved in place over inlet port 245. Electrode 244*b* is resident in preloading chamber 243, and another set 244*c*, is fixed in or near the wall of the main microchannel column 210 opposite inlet port 245. A third electrode 244*a* located in supply reservoir 241 is available to establish electrophoretic flow from the reservoir into compartment 243 and out into inlet port 245. One or more of these side compartments 240 may be connected to a front-end collector (not shown) which introduces analyte material gathered from the surrounding environment into one of preloading chambers 243. Remaining side compartments 240 store various reagents or chemical or biologically active species.

Finally, a vesicle fusing chamber 260 would be optionally included between vesicle loading compartments 240 and unloading chamber 230. Vesicle fusing chamber 260 would include processing chamber 263, two or more field electrodes 264*a* and 264*b* for inducing membrane fusion between two or more vesicles, and a short channel 265 connecting fusing chamber 260 with microchannel column 210 and unloading chamber 230.

Vesicles 205 would be moved through dedicated channel 210 in fluidic network 200, either electrically or under pressure, to specific locations along channel 210 for loading materials via electroporation through the vesicle membrane. Moreover, each of the structures comprising fluidic network 200 would be filled with a carrier buffer solution such as PBS (pH 7.4) together with optional amounts of sugars in order to maintain a specific solution chemistry and conductivity to facilitate vesicle integrity, membrane consistency, and osmotic balance across the bilayer membrane. Impedance measurements will be used to monitor electroporation progress, to interrogate the contents of vesicles, and to track the location of vesicles in the network. As containers, the vesicles prevent a sample from being diluted and provide a means for greatly reduced mixing and reacting volumes and rates. Moreover, as substrates, vesicles are ideal for fast surface-dominated reactions required in the preparation of any assay.

Figure 7A:
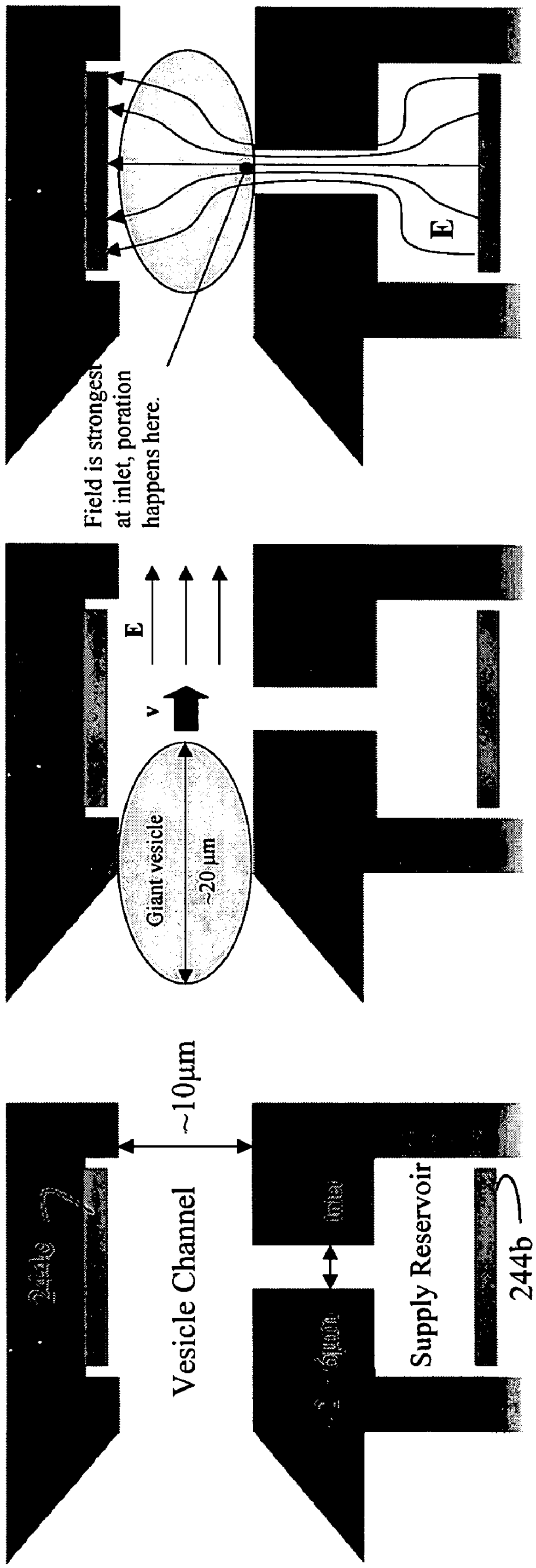
FIG. 7A illustrates a schematic of the process of electroporation at a typical inlet port of the present microfluidic system.
Figure 7B:
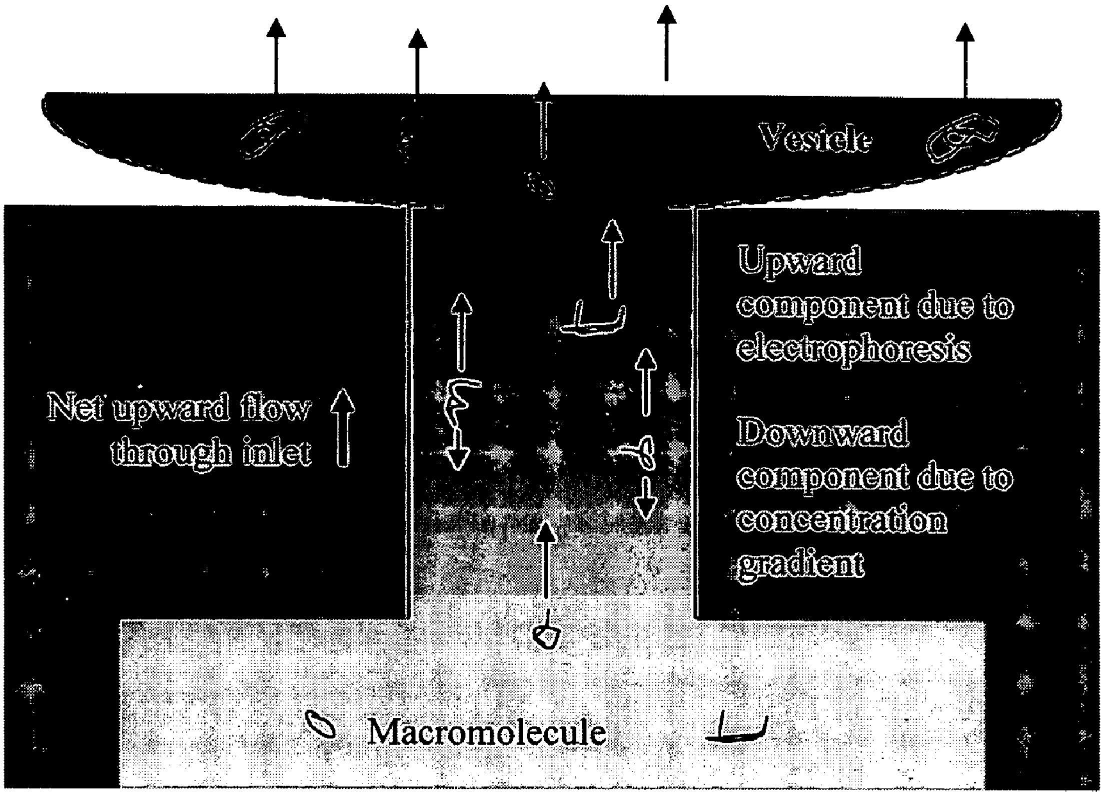
FIG. 7B illustrates the details of the electroporation process showing vesicle contact at the inlet port and transfer of molecules across the vesicle wall.

A loading site is designed to allow a single vesicle to come in contact with a loading inlet where electrodes to either side of the vesicle measure its presence as a change in impedance (FIGS. 7A and 7B). Once the presence of the vesicle is confirmed an agent is introduced into the vesicle by electroporation using the same set or another set of electrodes. The introduced agent may be the unknown trace specie under investigation or one of the various reagent materials. As shown in FIG. 7A, the process of rendering the vesicle permeable is ideally localized to only that region of the vesicle membrane in contact with and covering the loading inlet and allows molecules to be introduced into the vesicle interior or inserted into the bilayer membrane itself.

Molecules may be loaded through the porous membrane into the aqueous intra-vesicular space by mechanism of diffusion (based on molecular concentrations). In addition, molecules may be loaded through the porous membrane into the aqueous intra-vesicle space by electrophoresis (based on molecular charge and field intensity). In this case, the same electrodes used to electroporate the membrane may also serve to provide electric fields that act upon molecules loading into the vesicle. Compounds may be driven against concentration gradients to produce interior concentrations higher or lower than the fluid media surrounding the vesicle. In this manner a sample may be further concentrated and will not lose appreciable concentration until unloaded from the vesicle in the detection phase.

Once loaded with a sample, each individual vesicle can be sent through a series of loading compartments that use electroporation to introduce chemicals and enzymes for reactions. Different recipes may be used with different vesicles to run a full analysis of a sample. If desired, electrofusion of vesicles can be used to share information and induce metered chemical mixing.

Loading and Concentrating

Loading stations are locations where one or more narrow fluidic channel(s), or inlet(s), meet the vesicle channel. Samples or reagents may be supplied only from an inlet channel. Loading or unloading of compounds into a vesicle takes place when a vesicle is stopped with its membrane adjacent to an inlet channel.

Compounds may be loaded into a vesicle using electroporation of the vesicle membrane. Compounds are able to pass through the membrane during and shortly after being subjected to an electric field. Compounds may be allowed to diffuse into and out of a vesicle during electroporation.

Electroporation pulse parameters may be altered to encourage larger or smaller pore formation to limit transmembrane diffusion to compounds of certain size. In this case, small molecules may diffuse through the membrane out of the vesicle while ensuring the sample (e.g. macromolecules) does not escape.

Compounds may be forced into or out of a vesicle volume with electrophoresis. The same electrodes used to electroporate a vesicle can be used to induce movement of compounds along the electric field axis with the same or additional pulses. Compounds may be forced to move against their concentration gradient to create an intra-vesicular concentration higher or lower than that dictated strictly by diffusion.

Charged or polarizable compounds held within a preloading chamber may be prevented from diffusing into the adjoining vesicle channel by applying an electric field to drive compounds back into the chamber. This dc offset may be used in conjunction with a small ac signal to monitor vesicle impedance.

An imbalance in dissolved solute concentrations between the inside and outside of a vesicle will lead to osmosis of water across the bilayer membrane. Osmosis will attempt to balance concentrations on either side of the membrane and will lead to a change in water volume within the vesicle. Altering solute concentrations inside or outside a vesicle may be used to alter vesicular volume, change overall compound concentrations within the vesicle, or induce vesicle rupture.

Compounds may be loaded with electroporation into vesicles for reactions. Reactions would be confined to the volume within a vesicle. Reactants may include, but are not limited to, proteins (enzymes), solvents, denaturing agents, surfactants, and fluorescent dye molecules.

Vesicles can be fused together via electrofusion to share their constituents and initiate metered chemical reactions (See C. Ramos, et al., *Biochimie,* 2000, v. 82, pp. 511-518).

Moving and Sorting

Reagent compounds may be moved to different locations on-chip while contained within a vesicle. Vesicles may be moved with a pressure-flow, either with a pump external to the chip or with a pump integrated as part of the chip. Vesicles may also be moved with an electric field gradient along the axis of intended movement. Electrophoresis may be used to apply force on charged (ionic, anionic, zwitterionic) species in the vesicle membrane or within an electroporated vesicular volume. Dielectrophoresis may be used to apply force on polarizable species in the vesicle membrane or within the vesicular volume. Electroosmosis may be used to move the bulk fluid surrounding vesicles, thereby carrying vesicles in plug flow. Dedicated vesicle channels designed to accommodate specific vesicle sizes will serve as conduits for vesicle movement.

Vesicles may be sorted by differences in mobility under an applied electric field. Charged or polarizable species in the vesicle membrane or within the vesicular volume could be subjected to electrophoresis or dielectrophoresis to induce vesicle movement. Vesicle size, vesicle charge, and solution pH may be chosen to alter vesicle mobility. Vesicle mobility may be determined by monitoring vesicle position for a known period of time under an applied electric field. Moreover, analyte samples may be tracked by monitoring the location of particular vesicles. A vesicle may be detected at chosen locations by measuring changes in electrical impedance between two electrodes on opposite sides of the vesicle.

Finally, vesicles can be lysed at any time to remove their constituents without damage of the constituents as a precursor for further concentration or preparation or for analysis outside the vesicle. The constituents inside the vesicle can be relocated, for example to a separation column, for analysis.

What is claimed is:

1. A system for rapidly mixing two or more chemical and/or biological reagent species, comprising:

a plurality of synthetically prepared vesicles, wherein said vesicles comprise an aqueous volume surrounded by a single phospholipid bilayer approximately 1-20 μm in diameter;

a microchannel column terminating at a first end in a vesicle supply reservoir, and at a opposite second end in an vesicle unloading chamber, wherein said vesicle supply reservoir comprises at least a first field electrode, and means for introducing a fluid, and wherein said unloading chamber comprise at least a second field electrode, and a discharge channel;

a plurality of branching compartments disposed along said microchannel column between said vesicle supply reservoir and said vesicle unloading chamber, wherein each of said branching compartments is in fluid communication with said microchannel column, and wherein each of said branching compartments comprise;

a separate preloading chamber;

a supply channel connecting said preloading chamber to a reagent supply reservoir;

a short, small diameter inlet port opposite said supply channel, and opening to said microchannel column;

at least two poration electrodes, wherein one of said poration electrodes is disposed in said preloading chamber, and another of said poration electrodes is disposed opposite said small diameter inlet port on, or near, or recessed into, an interior wall of said microchannel column; and means for inserting at least one chemical or biological specie into an individual vesicle; and means for moving said vesicles through said microchannel column and sequentially through each of said branching compartments.

2. The system according to claim 1, wherein said vesicles are unloaded by applying a voltage pulse of greater than 1 volt for more than 100 ms across the phospholipid bilayer and thereby lysing the vesicle.

3. The system according to claim 1, further comprising a microfluidic separation column in fluid communication with said discharge channel, said microchannel separation column, comprising a buffer reservoir at a first end of said separation column and a waste reservoir disposed at a second end of said separation column, wherein said vesicle unloading chamber is disposed between said first and second ends of said separation column proximate to said buffer reservoir, and wherein at least one separation electrode is disposed in each of said waste and said buffer reservoirs.

4. The system according to claim 1, further comprising a vesicle fusing chamber disposed between one of said branching compartments and said unloading chamber, and co-axial with said microchannel column, wherein said vesicle fusing chamber comprises at least two fusing electrodes disposed opposite one another and parallel to said microchannel column.

5. The system according to claim 1, wherein said branching compartments further comprise one or more chemical and/or biological agents selected from the list consisting of proteins, nucleotides, viruses, bacteria, antibodies, antigens, fluorophore tagged species, enzymes, reagents, and electrolyte solutions.

6. The system according to claim 1, wherein said means for inserting said at least one chemical or biological reagent species comprises forming a transient pore in said phospholipid bilayer of said individual vesicle.

7. The system according to claim 6, wherein forming a transient pore in said phospholipid bilayer comprises bring said individual vesicle into contact with said small diameter inlet port and applying a square or triangular voltage pulse to said poration electrodes, wherein said voltage pulse induces a voltage of about 200 mV to about a 400 mV across said phospholipid bilayer for a period of between about 10 ms to about 100 ms.

8. The system according to claim 6, wherein said means for inserting further comprises altering said pulse shape, amplitude and duration to provide larger or smaller pore formation in said phospholipid bilayer thereby controlling specie migration across said bilayer.

9. The system according to claim 1, wherein said means for moving comprises the application of an electric potential across said one and second field electrodes.

10. The system according to claim 1, further comprising means for tracking a reagent or an analyte sample through said microchannel column, wherein said means comprises sensing electrodes disposed in each of said vesicles supply reservoir, each of said reagent supply reservoirs, and said vesicle unloading chamber.

* * * * *